US00PP16526P2

(12) United States Plant Patent
Bergman

(10) Patent No.: US PP16,526 P2
(45) Date of Patent: May 9, 2006

(54) ***AZALEA* PLANT NAME 'BITTERSWEET'**

(50) Latin Name: *Rhododendron hybrida*
Varietal Denomination: Bittersweet

(75) Inventor: Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 70 days.

(21) Appl. No.: 11/049,225

(22) Filed: Feb. 1, 2005

(51) Int. Cl.
*A01H 5/00* (2006.01)

(52) U.S. Cl. ..... Plt./238

(58) Field of Classification Search ..... Plt./238
See application file for complete search history.

*Primary Examiner*—Kent Bell
(74) *Attorney, Agent, or Firm*—C. A. Whealy

(57) ABSTRACT

A new and distinct cultivar of *Azalea* plant named 'Bittersweet', characterized by its dark green-colored leaves that do not abscise during the cooling and forcing periods; uniform and outwardly spreading plant habit; freely branching habit; uniform and freely flowering habit; rapid flowering response; showy salmon orange-colored flowers; semi-double hose-in-hose flower form with numerous petals and petaloids; excellent postproduction longevity with plants maintaining good flower substance for about five to six weeks in an interior environment; and very good resistance to *Cylindrocladium* in inoculated trials.

2 Drawing Sheets

Botanical designation: *Rhododendron hybrida.*
Cultivar denomination: 'Bittersweet'.

BACKGROUND OF THE INVENTION

The present Invention relates to a new and distinct cultivar of *Azalea*, botanically known as *Rhododendron hybrida,* an evergreen greenhouse-forcing type *Azalea*, and hereinafter referred to by the name 'Bittersweet'.

The new *Azalea* is a product of a planned breeding program conducted by the Inventor in Alva, Fla. The objective of the breeding program is to create new *Azalea* varieties having uniform plant habit, profuse and uniform flowering response, dark green foliage, good foliage retention during the cooling and forcing periods, resistance to *Cylindrocladium* and excellent postproduction longevity.

The new *Azalea* originated from a cross-pollination made by the Inventor in February, 1995, in Alva, Fla., of a proprietary *Azalea* selection identified as code number YB-0242, not patented, as the female, or seed, parent with the *Azalea* cultivar Champagne, disclosed in U.S. Plant Pat. No. 9,131, as the male, or pollen, parent. The new *Azalea* was discovered and selected by the Inventor as a flowering plant within the progeny of the stated cross-pollination in a controlled environment in Alva, Fla., in December, 1997.

Asexual reproduction of the new *Azalea* by terminal cuttings taken in a controlled environment in Alva, Fla. since April, 1998, has shown that the unique features of this new *Azalea* are stable and reproduced true to type in successive generations.

SUMMARY OF THE INVENTION

The new *Azalea* has not been observed under all possible environmental conditions. The phenotype may vary somewhat with variations in environment such as temperature, daylength and/or light intensity without, however, any variance in genotype.

The following traits have been repeatedly observed and are determined to be the unique characteristics of 'Bittersweet'. These characteristics in combination distinguish 'Bittersweet' as a new and distinct cultivar:

1. Dark green-colored leaves that do not abscise during the cooling and forcing periods.
2. Uniform and outwardly spreading plant habit.
3. Freely branching habit.
4. Uniform and freely flowering habit.
5. Rapid flowering response; plants begin flowering about 25 days after cooling treatment.
6. Showy salmon orange-colored flowers.
7. Semi-double hose-in-hose flower form.
8. Excellent postproduction longevity with plants maintaining good flower substance for about five to six weeks in an interior environment.
9. Very good resistance to *Cylindrocladium* in inoculated trials.

In side-by-side comparisons conducted in Alva, Fla., plants of the new *Azalea* differed from plants of the female parent, the selection YB-0242, in the following characteristics:

1. Plants of the new *Azalea* were more outwardly spreading than plants of the selection YB-0242.
2. Flower form of plants of the new *Azalea* was semi-double hose-in-hose whereas flower form of plants of the selection YB-0242 was semi-double.
2. Flowers of plants of the new *Azalea* were salmon orange in color whereas flowers of plants of the selection YB-0242 were red in color.

In side-by-side comparisons conducted in Alva, Fla., plants of the new *Azalea* differed from plants of the male parent, the cultivar Champagne, in the following characteristics:

1. Plant habit of plants of the new *Azalea* was denser and more uniform than plant habit of plants of the cultivar Champagne.

2. Flowers of plants of the new *Azalea* were salmon orange in color whereas flowers of plants of the cultivar Champagne were light coral pink in color.

Plants of the new *Azalea* can be compared to the plants of the cultivar Promise, disclosed in U.S. Plant Pat. No. 11,920. However, in side-by-side comparisons conducted in Alva, Fla., plants of the new *Azalea* differed from plants of the cultivar Promise in the following characteristics:

1. Plants of the new *Azalea* were stronger and denser than plants of the cultivar Promise.
2. Flower form of plants of the new *Azalea* was semi-double hose-in-hose whereas flower form of plants of the cultivar Promise was double.
3. Flowers of plants of the new *Azalea* were salmon orange in color whereas flowers of plants of the cultivar Promise were light coral pink in color.

BRIEF DESCRIPTION OF THE PHOTOGRAPHS

The accompanying colored photographs illustrate the overall appearance of the new *Azalea*. These photographs show the colors as true as it is reasonably possible to obtain in colored reproductions of this type. Colors in the photographs may differ slightly from the color values cited in the detailed botanical description, which accurately describe the colors of the new *Azalea*.

The photograph on the first sheet comprises a side perspective view of a typical flowering plant of 'Bittersweet'.

The photograph on the second sheet is a close-up view of typical flowers and leaves of 'Bittersweet'.

DETAILED BOTANICAL DESCRIPTION

The aforementioned photographs and following observations and measurements describe plants grown in Alva, Fla. with three plants per 15-cm containers, in a polypropylene-covered shade house under commercial production conditions. During the production of the plants, day temperatures ranged from 13 to 38° C. and night temperatures ranged from 0 to 26° C. Plants were pinched at planting, pinched a second time about 12 weeks later, and then pinched a third time about 12 weeks after the second pinch. After sufficient flower bud development, plants were cooled at 3 to 5° C. for about four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart, 1995 Edition, except where general terms of ordinary dictionary significance are used.

Botanical classification: *Rhododendron hybrida* 'Bittersweet'.

Commercial classification: Evergreen greenhouse-forcing type *Azalea*.

Parentage:

*Female or seed parent.*—Proprietary selection of *Rhododendron hybrida* identified as code number YB-0242, not patented.

*Male or pollen parent.*—*Rhododendron hybrida* cultivar Champagne, disclosed in U.S. Plant Pat. No. 9,131.

Propagation:

*Type.*—By terminal vegetative cuttings.

*Time to initiate roots.*—Summer: About five weeks at temperatures of 24° C. Winter: About six weeks at temperatures of 24° C.

*Time to develop roots.*—Summer: About nine weeks at temperatures of 24° C. Winter: About eleven weeks at temperatures of 24° C.

*Root description.*—Fine, fibrous, and white in color.

*Rooting habit.*—Freely branching.

Plant description:

*Plant form and growth habit.*—Perennial, evergreen; uniform and outwardly spreading plant habit; broad inverted triangle; moderately vigorous to vigorous growth habit. Densely foliated. Uniform and freely flowering habit with numerous semi-double hose-in-hose flowers per plant.

*Branching habit.*—Freely branching; about six primary lateral branches develop after the initial pinch (removal of terminal apex); numerous secondary and tertiary branches develop after the sequential second and third pinches.

*Plant height, soil level to top of flowers.*—About 25 cm.

*Plant diameter, area of spread.*—About 44 cm.

*Lateral branch description.*—Length: About 20 cm. Diameter at base: About 5 mm. Internode length: About 2 cm. Strength: Very strong. Texture: Young: Pubescent, fine brown hairs. Mature: Woody; pubescent, fine brown hairs. Color: Young: 146A. Mature: Close to 165A.

*Foliage description.*—Arrangement: Alternate, single. Foliage retention: Very good foliage retention on plants of the new *Azalea* that have been in a box for six weeks during the cooling treatment. Length: About 4.4 cm. Width: About 2.2 cm. Shape: Mostly elliptic. Apex: Cuspidate. Base: Cuneate. Margin: Entire. Venation pattern: Pinnate. Texture, upper and lower surfaces: Leathery, tough, durable; smooth, glabrous. Luster, upper surface: Glossy. Luster, lower surface: Somewhat glossy. Color: Developing and fully expanded foliage, upper surface: Much darker green than 147A. Developing and fully expanded foliage, lower surface: Close to 147B. Venation, upper surface: Close to 147A. Venation, lower surface: Close to 147B. Petiole: Length: About 7.5 mm. Diameter: About 3 mm. Texture, upper and lower surfaces: Pubescent. Color, upper and lower surfaces: Close to 144A.

Flower description:

*Natural flowering season.*—Spring after sufficient cool period. If forced, plants typically flower about 25 days after a four-week cooling treatment; rapid flowering response. Flowers persistent.

*Flower arrangement.*—Flowers arranged singly at terminals with usually about four to six flowers per apex; uniform and freely flowering habit. Flowers face upward to mostly outward.

*Flower appearance.*—Semi-double hose-in-hose flower form with numerous petals and petaloids; salmon orange-colored flowers.

*Fragrance.*—None detected.

*Flower diameter.*—About 6.3 cm.

*Flower depth.*—About 3.4 cm.

*Postproduction longevity.*—Excellent postproduction longevity; under interior conditions, plants maintain good flower substance for about five to six weeks.

*Flower bud* (*before showing color*).—Length: About 1.2 cm. Diameter: About 7.5 mm. Shape: Ovoid. Color: Close to 144A.

*Petals/petaloids.*—Arrangement: Semi-double hose-in-hose flower form; two to three whorls of about 13 imbricate petals and petaloids fused at the base. Length, largest petal: About 4.4 cm. Width, largest petal: About 2.8 cm. Shape: Beyond fused base, spatulate with rounded apex. Margin: Entire; slightly undulate. Texture, upper and lower surfaces: Smooth, satiny. Color: When opening and fully opened, upper surface: Close to 39A to 39B. When opening and fully opened, lower surface: Slightly darker than 39B.

*Sepals.*—No sepals observed, all transformed into petaloids.

*Peduncles.*—Length: About 1.5 cm. Diameter: About 2.5 mm. Angle: Mostly upright. Strength: Flexible; strong. Texture: Very pubescent. Color: Close to 144A to 144B.

*Reproductive organs.*—Androecium: Quantity of stamens per flower: Two to five. Filament length: About 2.3 cm. Filament diameter: Less than 1 mm. Filament color: Close to 55B to 55C. Anther size: About 3 mm by 1 mm. Anther shape: Oblong; elongated. Anther color: Close to 59A. Amount of pollen: None observed. Gynoecium: Quantity of pistils per flower: One. Pistil length: About 3.1 cm. Style length: About 2.2 cm. Style color: Towards the apex, close to 55B; towards the base, close to 55D to 155D. Stigma shape: Triangular. Stigma diameter: Less than 1 mm. Stigma color: Close to 154D. Ovary color: Close to 144A; heavily whiskered.

*Seed/fruit.*—Seed and fruit development have not been observed.

Weather/temperature tolerance: Plants of the new *Azalea* have been observed to be very tolerant to rain and wind. Plants of the new *Azalea* have been observed to tolerate temperatures from 0 to 38° C.

Disease/pest resistance: In inoculated trials that were conducted in Alva, Fla. during the summers of 2001, 2002 and 2003, plants of the new *Azalea* have been observed to be very resistant to infection by *Cylindrocladium.* Plants have not been observed to be resistant to pests and other pathogens common to *Azaleas.*

It is claimed:

1. A new and distinct *Azalea* plant named 'Bittersweet', as illustrated and described.

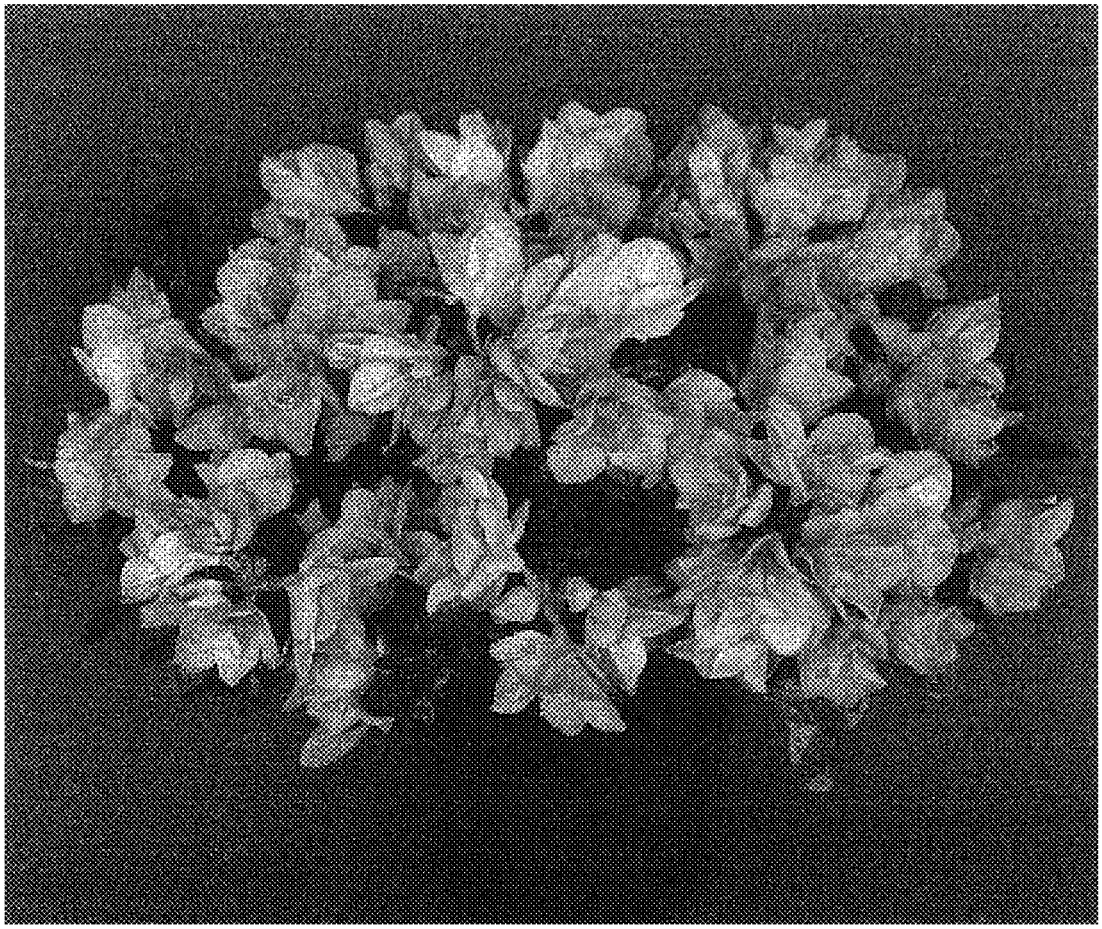

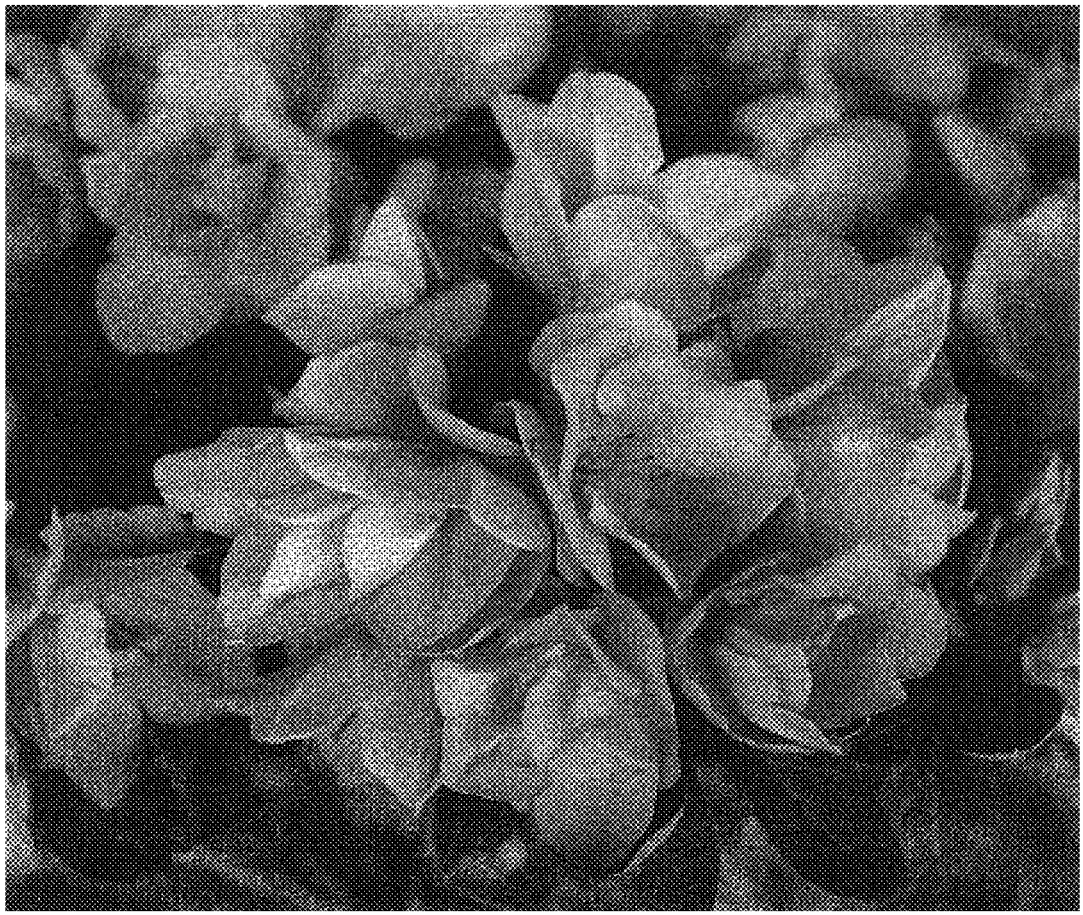

* * * * *